United States Patent [19]

Orjales-Venero et al.

[11] Patent Number: 5,256,665
[45] Date of Patent: Oct. 26, 1993

[54] PROCESS FOR PREPARING NEW 2-PIPERAZINYLBENZIMIDAZOLE

[75] Inventors: Aurelio Orjales-Venero; Neftalí Garcia-Dominguez; Victor Rubio-Royo; Rosa Rodes-Solanes, all of Vizcaya, Spain

[73] Assignee: Fabrica Espanola de Productos Quimicos y Farmaceuticos, S.A., Lejona, Spain

[21] Appl. No.: 946,012

[22] Filed: Sep. 15, 1992

Related U.S. Application Data

[63] Continuation of Ser. No. 735,931, Jul. 25, 1991, abandoned.

[30] Foreign Application Priority Data

May 10, 1991 [ES] Spain .................................. 9101147

[51] Int. Cl.$^5$ .................. A61K 31/495; C07D 403/04
[52] U.S. Cl. ..................................... 514/254; 544/366; 544/370
[58] Field of Search .................. 544/366, 370; 514/254

[56] References Cited

U.S. PATENT DOCUMENTS 4,877,878 10/1989 Kampe ................................ 544/366

OTHER PUBLICATIONS

Iemura et al., J. Med. Chem. 1986, 29, 1178–1183.
Iemura et al., CA105-97427s (1986).
Iemura et al., CA99-139971e (1983).

Primary Examiner—Cecilia Tsang
Attorney, Agent, or Firm—Davis Hoxie Faithfull & Hapgood

[57] ABSTRACT

A description is made of the preparation of new 2-piperazinylbenzimidazole derivatives, of general formula

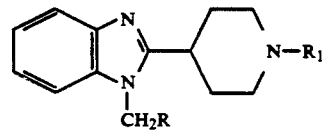

where R can be a hydrogen atom, a short chain alkyl group and a phenyl radical, substituted in position four by a halogen, and $R_1$ can be a hydrogen atom, an alkoxycarbonyl radical, a hydroxymethyl group and a diphenylmethyl group, and their addition salts with pharmaceutically acceptable acids.

These compounds are pharmacologically active as antagonists of the serotonin $5HT_3$ receptors.

4 Claims, No Drawings

PROCESS FOR PREPARING NEW 2-PIPERAZINYLBENZIMIDAZOLE

This is a continuation of copending application Ser. No. 07/735,931 filed on Jul. 25, 1991, now abandoned.

The present invention relates to a number of new 2-piperazinylbenzimidazole derivatives of formula (I), and their addition salts with pharmaceutically acceptable acids, a description being given of the method for preparing the same.

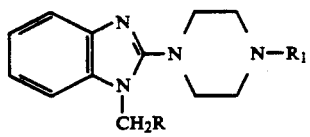
(I)

In formula (I) R is a hydrogen atom, a short chain alkyl radical, or a phenyl radical, substituted or not by a halogen in position 4, and $R_1$ es a hydrogen atom, a short chain alkoxycarbonyl radical, a hydroxymethyl group or a diphenylmethyl group. The short chain alkyl group is a carbonated radical with one to three carbon units, both linear and branched; the short chain alkoxyl group is an $OR_2$ residuum where $R_2$ has the same meaning previously attributed to a short chain alkyl group; a halogen is fluorine, chlorine, bromine or iodine. Likewise comprised in this invention are the addition salts of these compounds with inorganic acids, such as hydrochloric, hydrobromic, phosphoric and sulphuric acids, and organic acids such as acetic, fumaric, tartaric, oxalic and benzoic acids.

The process for preparing the said compounds basically comprises reacting a halogenated derivative of general formula

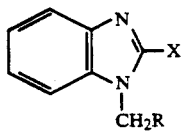
(II)

where R can be hydrogen, a short chain alkyl group and a phenyl radical, substituted or not in position four by a halogen, and X is a halogen, preferably chlorine, with a piperazine derivative, of general formula

(III)

where $R_1$ can be a hydrogen atom, an alkoxycarbonyl radical and a diphenylmethyl group.

Reaction takes place on mixing equimolecular amounts of reagents (II) and (III), allowing a surplus of piperazine (III) that can even be of 5 to 1 with regard to the halogenated derivative (II), and heating the reagent mixture at between 80° and 150° C. for a time interval of between five and thirty minutes.

The halogenated derivatives (II) and the piperazines (III) used in the reaction are known products and can be conventionally prepared.

The pharmacological activities of the compounds mentioned herein become clear by testing with animals using well established pharmacological processes. Two of the tests made are mentioned to illustrate this:

a) Wistar rats of both sexes, weighing 180–220 g, were anaethesized with urethane (1.25 g/kg, i.p.), subsequently subjected to trachea, carotid artery and jugular vein cannulation, with spontaneous breathing and a rectal temperature of 37°–38° C. On establishing the arterial pressure parameters (AP) and cardiac frequency (CF), the Bezold-Jarisch reflex was induced by means of a fast intravenous injection of 80 μg/kg of the serotonin-creatinine sulphate complex. Ten minutes later, and upon restoring the CF and AP to constant levels, the products claimed herein were injected intravenously and after five minutes intravenous injection of the serotonin-creatinine sulphate compound was repeated, quantifying inhibition of the Bezold-Jarisch reflex.

All the compounds tested proved to be active when administered intravenously within the range lying between 0.3 and 10 μg/kg, therefore proving to be antagonists of the serotonin $5HT_3$ receptors.

b) The inhibition of cisplatinum induced vomit in a conscious dog was studied. The products were administered intravenously 30 minutes before and 2 hours after the cisplatinum (3 mg/kg intravenously, 1 ml/kg). The number of emetic episodes were counted for five hours after administering the cisplatinum. The products hereof were more active than methochloramide in preventing cisplatinum induced vomit.

The results of these tests show that the compounds of the invention antagonize the action of serotonin at the $5HT_3$ receptors level and are therefore appropriate for preventing vomit induced by anticancerous agents, such as cisplatinum and radiations, and are potentially useful in prophylaxis and treatment of migraine, anxiety and other neuralgic disorders.

The following examples provide more details of the invention, without same being in any way confined thereto.

EXAMPLE 1

Preparation of 1-methyl-2-(1-piperazinyl)-1H-benzimidazole

A mixture of 5 g (30 mmol) of 2-chloro-1-methyl-1H-benzimidazole and 12.9 g (150 mmol) of anhydrous piperazine was heated at 125° C. for 15 minutes. The reagent mixture was provided with a 10% NaOH aqueous solution and extracted with dichloromethane (3×20 ml). The organic extracts obtained were dried on anhydrous sodium sulphate. After distilling the solvent in a vacuum, an oil was obtained that upon treatment with ether provided 4.5 g (69% yield) of a white solid, characterized as 1-methyl-2-(1-piperazinyl)-1H-benzimidazole, with a melting point of 80°–2° C.

The following were similarly prepared:

1-Phenylmethyl-1-(1-piperazinyl)-1H-benzimidazole. MP: 125°–7° C.

1-(4-Fluorophenylmethyl)-2-(1-piperazinyl)-1H-benzimidazole. MP: 84°–6° C.

1-Ethyl-2-(1-piperazinyl)-1H-benzimidazole. MP (fumarate): 170°–2° C.

1-Propyl-2-(1-piperazinyl)-1H-benzimidazole. MP (fumarate): 175°–7° C.

EXAMPLE 2

Preparation of 1-methyl-2-[(4-ethoxycarbonyl)-1-piperazinyl]-1H-benzimidazole

A mixture of 3.3 g (20 mmol) of 2-chloro-1-methyl-1H-benzimidazole and 3.2 g (20 mmol) of 1-ethoxycarbonylpiperazine was heated for 25 minutes at 120° C. The reagent mixture was provided with a 10% NaOH aqueous solution and extracted with dichloromethane (3×20 ml). The organic extracts were gathered, dried with anhydrous sodium sulphate and the solvent was eliminated at diminished pressure. 4.8 g (84% yield) of the product was obtained as a white solid that was purified by column chromatography, using dichloromethane/methanol (95/5) as eluent. MP: 122°-4° C.

The following were similarly prepared:

1-Methyl-2-[(4-diphenylmethyl)-1-piperazinyl]-1H-benzimidazole. MP (fumarate): 123°-5° C.

1-Phenylmethyl-2-[(4-diphenylmethyl)-1-piperazinyl]-1H-benzimidazole. MP (fumarate): 155°-8° C.

EXAMPLE 3

Preparation of 1-methyl-2-[(4-hydroxymethyl)-1-piperazinyl]-1H-benzimidazole 0.5 g of aluminium and lithium hydride were suspended in 75 ml of dry ether. 4.3 g (15 mmol) of 1-methyl-2-[(4-ethoxycarbonyl)-1-piperazinyl]-1H-benzimidazole were added slowly, stirring for ten hours at room temperature. This was hydrolized with 20 ml of water and 10 ml of 10% NaOH aqueous solution. The alkaline hydroxides precipitated by filtration were separated and the filtrate extracted with 3×20 ml of dichloromethane. The organic extracts were dried with anhydrous sodium sulphate and the solvent was eliminated in a vacuum. 3.4 g of an oil remained, that was purified by column chromatography, using dichloromethane/methanol (9/1) as eluent, obtaining 1.8 g (50% yield) of the above-mentioned product. MP: 82°-5° C.

What is claimed is:

1. 1-methyl-2-[(4-ethoxycarbonyl)-1-piperazinyl]-1H-benzimidazole.

2. 1-methyl-2-[(4-diphenylmethyl)-1-piperazinyl]-1H-benzimidazole.

3. 1-phenylmethyl-2-[(4-diphenylmethyl)-1-piperazinyl]-1H-benzimidazole.

4. A method of inhibiting vomiting induced by anticancerous agents comprising antagonizing the action of serotonin at serotonin receptors by administering an effective amount of a compound selected from the group consisting of 1-methyl-2-(1-piperazinyl)-1H-benzimidazole, 1-phenylmethyl-2-(1-piperazinyl)-1H-benzimidazole, 1-(4-fluorophenylmethyl)-2-(1-piperazinyl)-1H-benzimidazole, 1-ethyl-2-(1-piperazinyl)-1H-benzimidazole, 1-propyl-2-(1-piperazinyl)-1H-benzimidazole, 1-methyl-2-[(4-ethoxycarbonyl)-1-piperazinyl]-1H-benzimidazole, 1-methyl-2-[(4-diphenylmethyl)-1-piperazinyl]-1H-benzimidazole, 1-phenylmethyl-2-[(4-diphenylmethyl)-1-piperazinyl]-1H-benzimidazole, and 1-methyl-2-[4(4-hydroxymethyl)-1-piperazinyl]-1H-benzimidazole, or a pharmaceutically acceptable salt thereof.

* * * * *

UNITED STATES PATENT AND TRADEMARK OFFICE
CERTIFICATE OF CORRECTION

PATENT NO.   :   5,256,665
DATED        :   October 26, 1993
INVENTOR(S)  :   Aurelio Orjales-Venero et al.

It is certified that error appears in the above-identified patent and that said Letters Patent is hereby corrected as shown below:

On the title page, Abstract, contains the following incorrect formula:

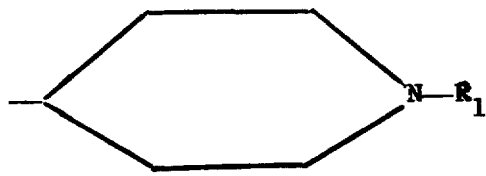

The correct formula is as follows:

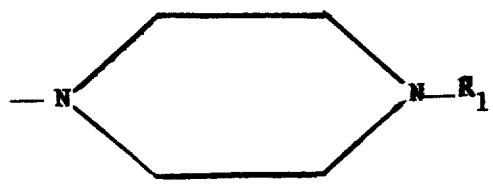

Signed and Sealed this

Fourth Day of October, 1994

Attest:

BRUCE LEHMAN

*Attesting Officer*   *Commissioner of Patents and Trademarks*